United States Patent [19]

Scharnberg et al.

[11] Patent Number: 4,693,720

[45] Date of Patent: Sep. 15, 1987

[54] DEVICE FOR SURGICALLY REPAIRING SOFT TISSUES AND METHOD FOR MAKING THE SAME

[75] Inventors: Lorne C. Scharnberg, Des Moines, Iowa; Deva Devanathan, Warsaw, Ind.

[73] Assignee: Katecho, Incorporated, Des Moines, Iowa

[21] Appl. No.: 779,068

[22] Filed: Sep. 23, 1985

[51] Int. Cl.⁴ ..................... A61F 2/02; A61B 17/04; A01N 1/02
[52] U.S. Cl. ..................................... 623/11; 623/66; 427/2; 128/334 R
[58] Field of Search ............... 128/156, 334 R, 335.5; 623/1, 2, 11, 15, 66, 13; 427/2

[56] References Cited

U.S. PATENT DOCUMENTS

| | | | |
|---|---|---|---|
| 2,671,444 | 3/1954 | Pease | 128/334 R |
| 3,124,136 | 3/1964 | Usher | 128/334 R |
| 4,268,468 | 5/1981 | Esper et al. | 264/131 |
| 4,329,743 | 5/1982 | Alexander | 623/13 |
| 4,338,926 | 7/1982 | Kummer et al. | 623/16 X |
| 4,347,847 | 9/1982 | Usher | 128/334 R |
| 4,411,027 | 10/1983 | Alexander | 623/11 |
| 4,520,821 | 6/1985 | Schmidt | 128/334 R |

OTHER PUBLICATIONS

Taylor et al., "Long Term Effects of Carbon on Soft Tissues", *The Journal of Bone and Joint Surgery*, vol. 1, 1982.
S. Saha, et al., "Comparative Study of Carbon and Graphite Cloth with Marlex and Dacron Mesh in the Repair of Abdominal Wound Defects", believed to have been published in 1981 or 1982.
C. Johnson-Nurse et al. "The Use of Flexible Carbon Fibre in the Repair of Experimental Large Abdominal Incision Hernias", *Br. J. Surg.*, vol. 67 (1980).

*Primary Examiner*—Richard J. Apley
*Assistant Examiner*—Alan W. Cannon
*Attorney, Agent, or Firm*—Zarley, McKee, Thomte, Voorhees & Sease

[57] ABSTRACT

The present invention comprises a flexible planar sheet having perimetric edges, the sheet being formed from a plurality of multi-fiber carbon filaments. The sheet is coated with a first solution of biodegradable polymer dissolved in a solvent, and the solvent is permitted to evaporate thereby leaving a first film of biodegradable polymer on the flexible sheet member. A second solution is applied to the sheet and contains a biodegradable polymer dissolved in a solvent, the concentration by weight of the polymer with respect to the solvent being greater in the second solution than in the first solution. When the solvent of the second solution evaporates it leaves a second film of biodegradable polymer on the planar sheet adjacent to the perimetric edges thereof. An alternative method of applying the polymer to the sheet is to lay polymer strips on the sheet and to apply heat to those polymer strips.

2 Claims, 4 Drawing Figures

DEVICE FOR SURGICALLY REPAIRING SOFT TISSUES AND METHOD FOR MAKING THE SAME

BACKGROUND OF THE INVENTION

This invention relates to a device for surgically repairing soft tissues and a method for making the same.

Certain problems are encountered in attempting to surgically repair soft tissue. The term "soft tissue" refers to tissue located between the skin (but not the skin itself) and organs or bone. An example of a situation where repair of soft tissue is accomplished is in the repair of a hernia.

Prior devices utilized for repairing soft tissue include various types of mesh material or woven fabric which are stitched in covering relation over the area to be repaired. Various types of substances have been used for these fabrics including steel, Nylon ®, Teflon ®, Dacron ®, and polypropylene. These materials have been used in a woven fabric or mesh, particularly for hernia repairs, for many years.

These various meshes have several disadvantages. Steel mesh does not have a flexible characteristic similar to the flexibility of the body, and therefore it feels uncomfortable during flexing or movement of the body. Furthermore, the steel does not decompose over a period of time.

Nylon ® has been used, but this material has a very slight hostility to the body. As a result, the body does not form satisfactory tissue growth around the nylon ® so as to provide a natural healing of the hernia or injury.

Polypropylene is relatively inert to the body, but does not have a sufficient strength for use over a period of time. The new growth tissue encapsulates the polypropylene but is fairly thin and grows in a disorganized manner. After several years of flexing, the polypropylene sometimes will fracture and the fibrous tissue which has formed over the polypropylene is not sufficiently strong to prevent a reoccurrence of the hernia.

Therefore a primary object of the present invention is the provision of an improved device for surgically repairing soft tissues and a method for making the same.

A further object of the present invention is the provision of an improved device which has improved tensile strength over devices previously used.

A further object of the present invention is the provision of an improved device which stimulates fibrotic tissue growth in an organized pattern so that the fibrotic tissue growth eventually will support the hernia or injury independently of the fabric which forms the device.

A further object of the present invention is the provision of a device which when stitched to the body has a flexibility which is compatable with the body so as to minimize discomfort to the patient.

A further object of the present invention is the provision of a device which when stitched to the body is of light weight so as to minimize discomfort to the patient.

A further object of the present invention is the provision of a device which permits the body to heal itself so that when the device itself breaks or decomposes, the fibrous tissue formed by the body will maintain the repair.

A further object of the present invention is the provision of a device which stimulates fibrotic tissue growth quickly so that the fibrotic tissue is self repairing within approximately sixty to ninety days after application of the device.

A further object of the present invention is the provision of a device which is economical to manufacture, durable in use, and efficient in operation.

SUMMARY OF THE INVENTION

The present invention comprises a fabric material formed from a woven filamentous carbon. The fabric is formed from a plurality of woven filaments or strands, each comprising a plurality of carbon fibers. These filamentous carbon filaments or strands are commercially available and include various numbers of fibers per strand or filament, usually in multiples of 1000 fibers. Various numbers of fibers per strand or filament may be used, and various multiples of 1000 fibers per strand may be used, without detracting from the invention. The strands or filaments are usually twisted, but they may be twisted or untwisted and the particular number of twists per inch is not critical to the invention. An example of a preferred strand or filament is manufactured by Union Carbide Corporation under the yarn designation "Thornel" 300, and under the catalog number X0535. In this preferred embodiment the filaments or strands each include approximately 1,000 carbon fibers and each strand or filament is twisted at the rate of approximately one-half turns per inch.

The filaments or strands are woven into a fabric material. Various types of weaves may be used such as satin weaves or others. The preferred weave is a plain weave where the filaments or strands are interwoven with the warp in one direction and the weave in a direction at right angles to the warp.

Carbon strands or filaments are sometimes commercially marketed with a sizing material on them. For example, the "Thornel" 300 filaments are marketed with an epoxy on them which is at least partially toxic to the human body. Other filamentous carbon filaments may come with other sizing materials on them or with no sizing at all.

If the filaments or strands have sizings on them, it is necessary to remove the sizing so as to minimize any toxicity to the body. This is done after the filaments or strands have been woven into a mesh fabric, and is accomplished by applying a suitable solvent such as methyl ethyl ketone (MEK), toluene, or other solvents to remove the epoxy or other applicable sizing.

In the preferred method for removing the commercial sizing from the filaments or strands, the solvent is applied twice to remove as much epoxy or other applicable sizing as possible. The filaments or strands are then heated at approximately 400° C. for approximately 30 minutes to burn off the remaining residues of epoxy or other applicable sizing. After heating, the strands are rinsed again in the solvent.

After removal of the epoxy or other applicable sizing, the carbon filaments are slick, and they will not retain their position in the woven fabric very well. It is therefore necessary to apply a new sizing which is not toxic to the human body.

Various biodegradable and biocompatible polymers may be used for sizing. The primary requirements are that they (1) be capable of being metabolyzed or hydrolyzed by the body and (2) be inert and non-toxic to the body so that they will not inhibit fibrous tissue growth. The preferred material for applying sizing to the fabric is polycaprolactone (PCL) manufactured by Union Carbide under the product designation "Tone" P-700 polymer. The PCL comes in pellets and is dissolved in a solvent of toluene manufactured by J. T. Baker Company, Phillipsburg, N.J.

A first solution of PCL and toluene is made by mixing PCL in a first solution having a concentration of from 0.1% to 5% by weight of PCL with respect to toluene. The preferred concentration is, 0.2% by weight of PCL to toluene. The entire fabric sheet is dipped into this solution so as to apply the PCL to the fabric for sizing. The fabric is then permitted to dry so that the toluene evaporates. The use of toluene is important because it evaporates and leaves no noticable traces on the carbon. The residue left on the carbon after evaporation of the toluene is the PCL which is compatible with the body and which will hydrolyze within the body over a period of time.

A second solution comprising from 5% to 30% by weight PCL in toluene is used to apply an edging to the flexible sheet material. The preferred concentration for this purpose is 20% by weight PCL to toluene. The edges of the sheet material are dipped in this solution and the toluene is permitted to evaporate.

This process deposits a heavier solution of PCL on the edges of the sheet material so that the edges are stronger and more able to support stitches or sutures when the device is surgically implanted in a patient.

The polymer sizing and/or edging can be applied by an alternative method wherein polymer strips are laid on the woven fabric and heat is applied to cause the polymers to melt and form on the strands or filaments in the fabric.

When the carbon mesh material treated with the PCL is surgically implanted in a patient, the edges of the carbon sheet material are strong and are capable of holding the stitches or sutures in place when the device is surgically implanted. The carbon has the effect of stimulating fibrotic tissue growth in the body. Fibrous cells encapsulate each of the 1000 fibers within each of the strands or filaments of carbon. Furthermore the fibrous cells are elongated and are oriented in a linear fashion in the direction of the strands. Because the carbon fabric includes strands or filaments going in directions perpendicular to one another, the fibrous tissue growth also grows in two directions thereby creating a strong fibrous repair of the injury.

Figure 1:
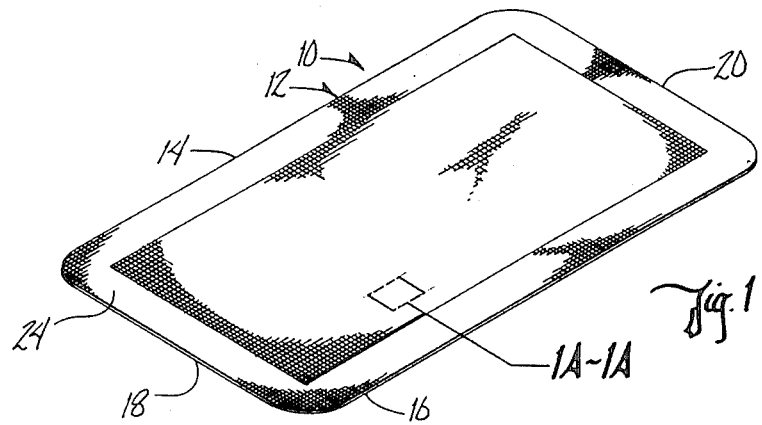
FIG. 1 is a perspective view of the device of the present invention.
Figure 1A:
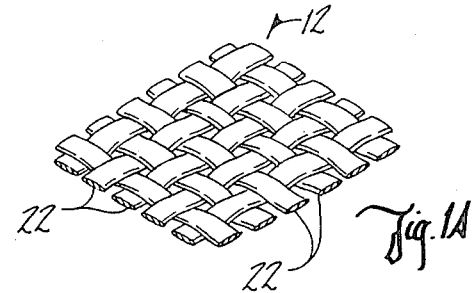
FIG. 1A is an enlarged detailed view showing the arrangement of the fiber strands.

Referring to the drawings, the numeral 10 refers generally to the device of the present invention. Device 10 includes a sheet member 12 having opposite perimetric edges 14, 16 and 18, 20.

Sheet member 12 comprises an interwoven fabric made from a plurality of filamentous carbon strands or filaments 22 which are preferably woven in a plain weave at right angles to one another. Other weaves may be used, but the plain weave is preferred because the fibrous tissues which form along the carbon fibers of each strand or filament generally run in the directions of the filaments. Therefore by having the strands or filaments run at right angles with respect to one another, the present invention causes the fibrous tissue to form in a lattice work which extends in the two perpendicular directions of the strands or filaments. This results in a very strong fibrous tissue being formed.

An example of a filamentous carbon filament or strand used for the present invention is manufactured by Union Carbide Corporation under the trade designation Thornel ® 300. This filamentous carbon strand includes approximately 1000 fibers per strand. Each strand is twisted approximately one half twist per inch. When purchased commercially each strand is coated with an epoxy sizing which is toxic to the human body.

The filaments or strands 22 are woven into the fabric which has an approximate thickness of 7/1000 of an inch and which has a weight of approximately 3.77 ounces per square yard.

Because the epoxy which surrounds the filaments is toxic to the human body, it is necessary to remove this epoxy before producing device 10. Therefore the fabric with the toxic epoxy thereon is submerged in a solution of methyl ethyl ketone (MEK) which is used as a solvent to remove the epoxy. Other suitable solvents such as toluene may be used. The device is dipped into a first solution of MEK and then is removed and permitted to dry. It is then submerged into a second solution of MEK and again permitted to dry. The fabric is then heated at 400° centigrade for approximately 30 minutes to burn away the remaining residues of the epoxy. Finally the fabric is again rinsed in MEK.

With the epoxy sizing removed, the woven carbon filaments or strands 22 are very slick, and the fabric is easily deformed in response to tension such as occurs when stitches are used to secure it in place. It is therefore necessary to apply a sizing to the fabric which is compatible with the human body.

Application of the sizing is accomplished by creating a first solution comprised of from, 0.1% to 5% by weight polycaprolactone (PCL) to toluene. The preferred concentration is 0.2% by weight of PCL to toluene. An example of a polycaprolactone which may be used is a product manufactured by Union Carbide Corporation under the trade designation "Tone" P-700 polymer. An example of a solvent which can be used is toluene manufactured by J. T. Baker Chemical Company, Phillipsburg, N.J. under the product designation No. 9462-3. Other solvents may be used so long as they evaporate without leaving trace residues on the fabric.

The fabric is submerged in the solution of PCL and toluene, and is removed. When the toluene evaporates, a thin coating of PCL is left on the outer surface of the fibers within the fabric.

Polymers other than polycaprolactone could be utilized for sizing the fabric, but it is important that these polymers be nontoxic to the body. Preferably these polymers should be polymers which will hydrolyze or metabolyze over extended periods of time when contained within the body after surgery.

In order to strengthen the edges of the sheet member 12 an edging 24 is provided around the perimetric edges of the sheet member. This edging is formed by dipping the edges of the fabric in a solution of 20 percent by weight PCL and 80% by weight toluene. This solution may range from 5% to 30% PCL to toluene. The toluene is then permitted to evaporate, thereby leaving a residue of PCL around the edges of the sheet member. This residue is more concentrated than the residue within the center portion of the sheet member which was formed by the 0.2 percent PCL solution.

The edging 24 provides a strong base to which stitches may be applied for securing the sheet member 12 surgically within the body. The provision of this edging is important since the filametous carbon without any sizing or edging will tend to pull apart and not hold. The device of the present invention is extremely strong in response to tension, and has a tensil strength which is 6 to 7 times greater than the tensile strength of polypropolene meshes presently used.

Figure 2:
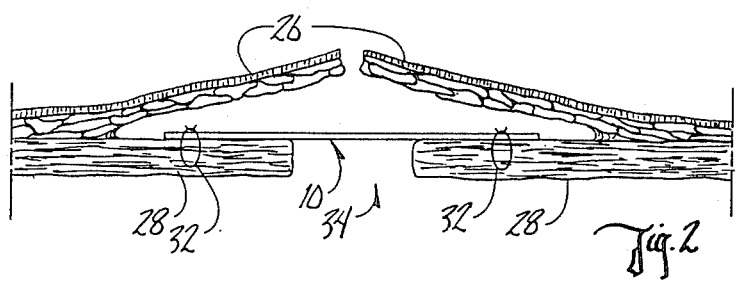
FIG. 2 is a sectional view showing one usage for the repair device of the present invention.
Figure 3:
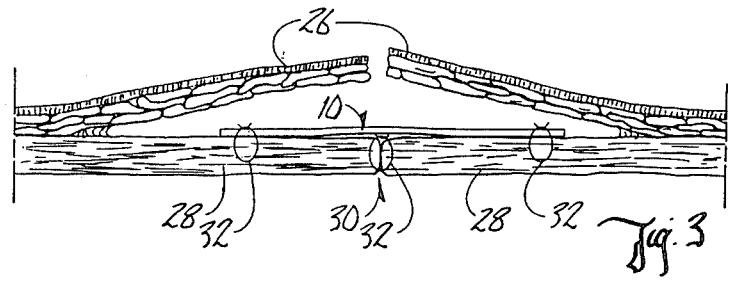
FIG. 3 is a view similar to FIG. 2 showing another usage for the repair device of the present invention.

FIGS. 2 and 3 illustrate the attachment of the device to a surgical opening within the body. The numeral 26 illustrates the skin layer and the numeral 28 indicates the soft tissue which requires repair. Device 10 is place over the damaged area 30 and is held in place by stitches 32 which extend through the edging 24 of sheet member 12. The device may be used to repair a small opening such as 30 shown in FIG. 3 or a large opening such as 34 shown in FIG. 2.

It has been found that within 30 to 60 days fibrous tissue forms along the many fibers of each filament or strand 22 within sheet member 12. During this period of time the sheet member 12 provides strong reinforcement to the damaged area. However, after this period of time the fibrous tissue formed by the body provides the primary strength for the opening. The PCL which coats the carbon filaments eventually hydrolizes and is carried away by the systems of the body. The carbon filaments after a period of time will break up, but because they are not alien to the body they do not provide any damage or adverse effects to the body. Because the perpendicular direction of the filamentous carbon strands, the fibrous tissues formed by the body are also formed into a lattice work of perpendicularly extending fibrous tissues, thereby creating a very strong natural repair for the injured portion of the body.

The sheet member 10 is very light, and has flexible characteristics which are similar and compatible to the body. Therefore a minimum of discomfort is encountered as compared to the discomfort which occurs with the use of other types of materials for repairing hernias. Furthermore, since the tissues quickly repair the body and provide the primary support to the injured area, eventual breakdown of the carbon filaments does not result in a reopening of the injury.

With other meshes that have been used, particularly the polypropolene mesh, a thin encapsulation of unorganized fibrotic growth forms around the mesh. The integrity of the repair is only as good as the flex life of the mesh. On occasion these meshes fracture, and the patient has another hernia. With the present invention this is not as likely to occur because the fibrous tissues of the patient form a permanent repair of the injury.

Thus it can be seen the device accomplishes at least all of its stated objectives.

What is claimed is:

1. A device for use in surgically repairing soft tissues of a living animal, said device comprising:

a flexible planar sheet having a plurality of perimetric edges extending around the perimeter thereof, said sheet being formed by at least first and second groups of strands, each of said groups of strands comprising a plurality of filamentous carbon strands;

each of said strands in said first group of strands extending generally in a first direction, and each of said strands in said second group of strands extending generally in a second direction from said first direction and being formed into an interwoven relationship with said strands of said first group of strands whereby said interwoven first and second groups of said strands combine to form said flexible planar sheet, wherein said first group of strands are interwoven in a regular weave with said second group of strands whereby said strands of said first group pass alternatively over and under adjacent strands of said second group and wherein said strands of said second group pass alternatively over and under adjacent strands of said first group;

a first film of biodegradable polymer coating said first and second groups of strands and holding said first and second groups of strands against relative movement therebetween so as to prevent unraveling of said interwoven relationship of said first and second groups of said strands;

a second film of biodegradable polymer coating said flexible planar sheet adjacent said perimetric edges thereof to form an edging strip extending completely around said perimetric edges of said planar sheet, said second film comprising a heavier concentration of said biodegradable polymer than said first film whereby said edging strip is sufficiently strong to support sutures when said device is surgically implanted in said animal;

said biodegradable polymer of said first and second films being substantially non-toxic to said living animal and being capable of hydrolyzing and metabolizing over an extended period of time after being surgically placed within said living animal;

said first and second films being the only material coating said flexible planar sheet, wherein said films are coated according to the method comprising:

applying a first solution to said planar sheet, said first solution comprising said biodegradable polymer dissolved in a solvent;

permitting said solvent of said first solution to evaporate, thereby leaving said first film of said polymer on said planar sheet;

applying a second solution to the perimetric edges of said flexible sheet, said second solution comprising said biodegradable polymer dissolved in a solvent in a greater concentration than the concentration of said polymer in said solvent of said first solution;

permitting said solvent in said second solution to evaporate, thereby leaving said second film of said biodegradable polymer to form an edging strip around said perimetric edges of said planar sheet.

2. The device of claim 1 made according to the method comprising forming said first solution with said polymer being in concentration of 0.1% to 5% by weight with respect to said solvent, and forming said second solution with said polymer in concentration of from 5% to 30% by weight with respect to said solvent.

* * * * *